United States Patent [19]

Patelski, III

[11] Patent Number: 4,989,274

[45] Date of Patent: Feb. 5, 1991

[54] SPORTS GOGGLES

[75] Inventor: Kazimir J. Patelski, III, Costa Mesa, Calif.

[73] Assignee: Sport Eyes Enterprises, Inc., Costa Mesa, Calif.

[21] Appl. No.: 435,711

[22] Filed: Nov. 13, 1989

[51] Int. Cl.⁵ .................................................. A61F 9/04
[52] U.S. Cl. ............................................. 2/436; 2/441
[58] Field of Search ................... 2/428, 429, 430, 426, 2/441, 443, 436, 437, 439, 447, 440

[56] References Cited

U.S. PATENT DOCUMENTS

| | | | |
|---|---|---|---|
| 2,556,847 | 6/1951 | MacLean | 2/436 |
| 4,764,990 | 8/1988 | Markert | 2/436 X |
| 4,910,806 | 3/1990 | Baker et al. | 2/428 X |

FOREIGN PATENT DOCUMENTS

WO79/00548  8/1979  PCT Int'l Appl. ............. 2/430

Primary Examiner—Peter Nerbun
Attorney, Agent, or Firm—Walter A. Hackler

[57] ABSTRACT

A sports goggle, for water sports, downhill skiing and other sports, comprises a frame having left and right vision openings and having anterior and posterior surfaces, the frame is floatable and is contoured and constructed of a resilient and flexible plastic or rubber material so as to enable the posterior surface to conform to a wearer's face. Included are left and right curved lenses which are sized and shaped for covering a respective one of the vision openings in the frame and which are constructed of a thin, transparent, shatter-resistant plastic polarized lens material. A plurality of stand-off mounting bosses are formed on the frame to project forwardly from the anterior surface around each vision opening, each mounting boss having a forwardly-opening recess therein. A like plurality of rearwardly-projecting pins are fixed to each lens, the pins being sized and located for inserting into corresponding recesses in the mounting bosses. Spacing bosses are formed on the frame intermediate at least some of the mounting bosses so that an air gap is assured between the lenses and underlying regions of the frame even when the frame is flexed to conform to a small-sized face, air flow through the gap keeping the lenses from getting fogged during use and enabling water drainage. A floatable resilient strap is connected to rearward ends of the frame for retaining the goggles on a wearer's head.

6 Claims, 1 Drawing Sheet

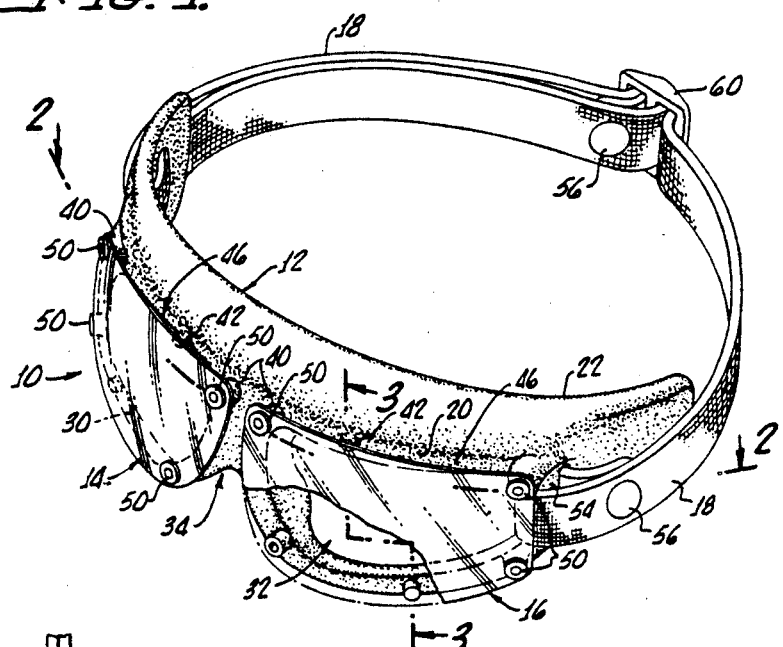
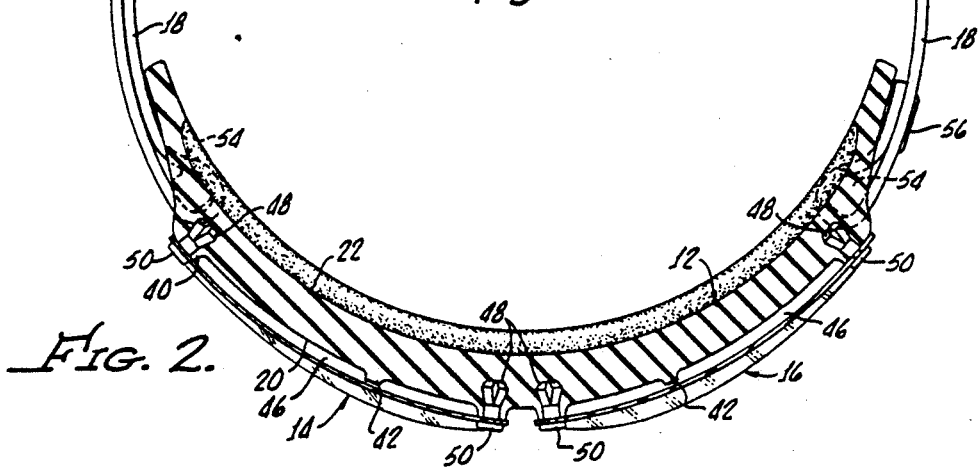
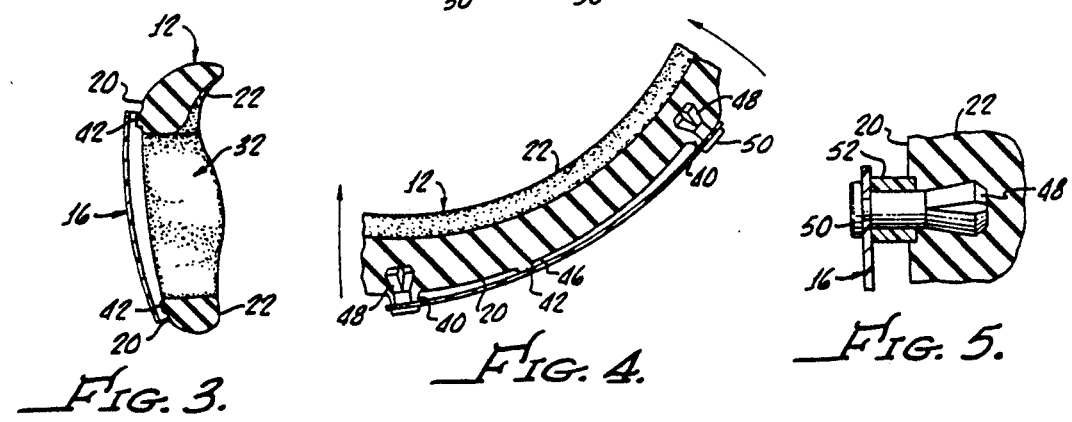
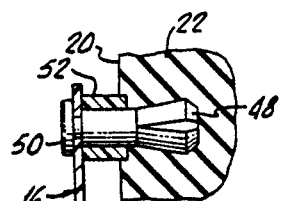

SPORTS GOGGLES

BACKGROUND OF THE INVENTION

1. Field of the Invention:

The present invention relates generally to the field of goggles worn for eye protection during the playing of sports and, more particularly, for sports goggles worn for water or down-hill skiing and the like.

2. Discussion of the Prior Art:

As is commonly known, at least to sports enthusiasts, a number of different types of sports goggles are available in sporting goods stores. Many of these sports goggles are of the tough, physically protective type, which are commonly used in such sports as hand ball and racquet ball, where there exists a high probability that eye injury can result if the eye is hit by a ball traveling at high velocity. Another common type of sports goggle is the underwater type, such as are used by scuba divers, long distance swimmers and racing swimmers, to keep water out of their eyes. Still another common type of sports goggle is the type used by skiiers. Normally this last type of sports goggle serves as much, at least to ordinary skiiers, as a fashion statement as an eye protector.

Still another type of sports goggle is the WW1 aviator type affected by many motorcyclists and race car drivers who disdain the wearing of helmets with full-face visors, to keep dust, dirt and the wind out of their eyes. A further type of sports goggle is the type worn by combatants in mock war games in which the combatants shoot at one another using blank cartridges or, more recently, using paint-ball firing guns.

A common problem with many types of sports goggles of the type which fit closely to the wearer's face is the fogging up of the inside surface of the lenses by the condensation thereon of moisture from the wearer's eyes and covered part of the wearer's face. This fogging up of the inside surface of the lenses becomes worse as the activity level of the wearer increases and the wearer perspires more. To reduce or eliminate such lens fogging, some types of goggles have ventilation holes formed in the frame. Typical of such type of goggles are safety goggles. Other types of sports goggles are constructed having miniature electric blowers to keep the inside of the lenses from fogging. Still other types use miniature electric heating elements to prevent lens fogging.

All of known types of sports goggles having antifogging lens provisions are too complicated and/or costly and/or do not perform satisfactorily. It is, therefore, a principal objective of the present invention to provide an improved sports goggle which incorporates means for preventing or, at least, substantially reducing lens fogging during use and which has the advantage of being reasonably priced and has the still further advantage of having user-replaceable lenses.

Another problem associated with goggles intended for water sports is the accumulation of water between the lens and the face of the wearer. Heretofore, available goggles which conform to the face to prevent water entry are unfortunately not always effective in that regard when the wearer is physically active, as in water skiing, wind surfing or jet skiing, and is subject to heavy water impact. In instances where water gets behind the lens, it is held there by the portion of the goggles which conform to the wearer's face.

The present invention overcomes this problem by enabling free drain of water from the face of the wearer behind the lens, while at the same time inhibiting water entry by means of a conforming frame.

SUMMARY OF THE INVENTION

In accordance with the present invention, there is provided a sports goggle for water skiing, jet skiing downhill skiing, wind surfing skiing and other sports, especially, but not necessarily, those sports in which water or snow spray is directed at the wearer's face. The present sports goggles are, of course, also useful for such diverse sports as hand ball, racquet ball, tennis, speed skating and the like.

Comprising the present sports goggles is a frame having vision openings, an anterior surface and a posterior surface, the frame being constructed of a resilient and flexible material, preferably a lightweight plastic or rubber, and preferably of a material which floats in water, the frame being sufficiently resilient to enable the posterior surface thereof to closely conform to the face of the user so as to seal the posterior surface of the frame to the wearer's face. The frame may include left and right vision openings.

The goggles include at least one detachable lens, and preferably two detachable lenses shaped and contoured to cover the vision openings in the frame. Preferably the lens or lenses are constructed of a thin, transparent, shatter-resistant plastic lens material. Combination lens attaching and primary lens spacing means are included for detachably attaching the lens or lenses to the anterior surface of the frame with the lens or lenses spaced forwardly therefrom and so that the lens or lenses cover both the left and right vision openings. There are additionally provided secondary lens spacing means for helping to maintain the lens or lenses, as the case may be, spaced forwardly of the anterior frame surface after the lens or lenses have been attached thereto, an air flow gap between the lens or lenses and underlying regions of the anterior frame surface being thereby always assured even when the frame flexes or is curved in a smaller radius to fit a wearer having a small face. Still further included in the goggles of the present invention is a resilient strap which is connected to the goggle frame for retaining the goggles on a wearer's head.

In accordance with a preferred embodiment of the invention, the combination lens attaching and primary lens spacing means include a plurality of mounting bosses projecting forwardly from the frame anterior surface in the region of the vision openings, the mounting bosses being formed having forwardly-opening recesses thereinto. Further included are a plurality of pins which extend rearwardly from a posterior surface of the lens or lenses, the pins being located and sized for being inserted into the recesses formed in the mounting bosses recesses to detachably attach the lens or lenses to the goggles frame.

Further, in accordance with the preferred embodiment, the secondary lens spacing means comprises a plurality of spacing bosses projecting forwardly from the frame anterior surface, the spacing bosses being positioned intermediate at least some of the mounting bosses.

When two lenses are provided, the combination lens attaching and primary lens spacing means comprise at least four mounting bosses for each of the lenses, the mounting bosses extending forwardly from the frame anterior surface around each of the vision openings, each of such mounting bosses being formed having a forwardly-opening recess. The combination lens attaching and primary lens spacing means further comprise rearwardly projecting attachment pins mounted to each of the two lenses in locations corresponding to the mounting bosses, the lenses being attached to the frame by the forced insertion of the pins into the mounting boss recesses.

It is preferred that there be two spaced apart upper and two spaced apart lower mounting bosses for each of the two lenses. In such case, the secondary lens spacing means preferably comprise at least two spacing bosses for each of the lenses, the spacing bosses projecting forwardly from the anterior surface of the frame with at least one of the spacing bosses being positioned between the two upper mounting bosses for each of the lenses and at least one of the spacing bosses being positioned between the two lower mounting bosses for each of the lenses.

Because the lens or lenses, as the case may be, are easily attached to and detached from the frame, different types of interchangeable lens or lenses may be used. For example, some lenses may be clear and other lenses may be shaded polarized and/or mirrored for sun and glare protection.

BRIEF DESCRIPTION OF THE DRAWINGS

The present invention can be more readily understood by a consideration of the following detailed description when taken in conjunction with the accompanying drawings, in which:

FIG. 1 is a partially cutaway perspective drawing of a pair of sports goggles in accordance with the present invention, showing the frame and detachable lenses and showing an elastomeric headband used to retain the goggles on a wearer's head;

FIG. 2 is a transverse cross sectional drawing, taken along line 2—2 of FIG. 1, showing the manner in which the lens are detachably mounted to an anterior surface of the goggles frame and showing the manner in which the lenses are spaced forwardly of such anterior surface so as to provide an air gap between the lenses and the frame;

FIG. 3 is a vertical cross sectional drawing taken along line 3—3 of FIG. 1 and showing the manner in which secondary lens spacers keep the lens spaced outwardly from the frame; and FIG. 4 is a transverse cross sectional drawing, taken in the plane of FIG. 2, showing the goggles frame flexed, for example, to fit a small persons's face and showing the lens still spaced forwardly of the anterior face of the goggles frame.

FIG. 5 is a transverse cross sectional drawing showing a separable boss for spacing each lens from the frame.

In the various Figures like elements and features are given the same reference number and/or other identification.

DESCRIPTION OF THE PREFERRED EMBODIMENT

There is depicted in FIG. 1 a pair of sports goggles 10 in accordance with the present invention. Comprising sports goggles 10 are a flexible, resilient-floatable frame 12, left and right thin, flexible plastic lenses 14 and 16, respectively, and an adjustable retaining strap or head band 18, the latter being attached to the frame as described below.

Frame 12, as shown in FIGS. 1-3, is contoured in shape to fit a typical wearer's face and is formed having an anterior (forward) surface 20 and a posterior (rearward) surface 22. Preferably frame 12 is constructed of a somewhat soft and pliable plastic, floatable material and posterior frame surface 22 is contoured such that when worn and held relatively tightly to a wearer's face (by strap 18) posterior surface 22 of the frame fits in a sealing relationship to the wearer's face. Consequently, frame 12 keeps perspiration and water running down the wearer's face out of the wearer's eyes.

Defined by frame 12 are left and right vision openings 30 and 32, respectively, which are sized and located so as to be forwardly of a wearer's eyes when goggles 10 are worn in a normal manner. Vision openings 30 and 32 are made sufficiently large so as not to unduly restrict a wearer's peripheral vision and so that the frame is not unnecessarily intrusive on a wearer's vision, thereby enabling near complete peripheral vision. Mask frame regions defining vision openings 30 and 32 curve upwardly in the nasal region of goggles 10 to form an arched bridge region 34 (FIG. 1) permitting the goggles to rest comfortably on the nose of a wearer.

Left and right lenses 14 and 16, respectively, are sized and shaped (including being contoured in a six base optically correct curve) and are detachably mounted to frame 12 so as to cover corresponding left and right vision openings 30 and 32 in frame 12 (FIG. 1). Although the use of two lenses 30 and 32, as shown in FIGS. 1 and 2 is preferred, it will be appreciated that only a single lens (not shown) may be used. In such case, the single lens would be sized and contoured, and attached to frame 12, so as to cover both frame viewing openings 30 and 32. Such a single lens would preferably be attached to frame 12 in the manner described below for attaching individual lenses 14 and 16 to the frame.

Frame 12 is formed having a number of forwardly-projecting primary and secondary lens spacing bosses 40 and 42, respectively, which function to space lenses 14 and 16 a short distance outwardly from underlying regions of frame 12 around vision openings 30 and 32, thereby creating an air gap 46 (FIGS. 1, 2, and 4). Preferably, bosses 40 and 42 project about ⅛ inch outwardly from frame anterior surface 20 so as to cause air gaps 44 and 46 to be nominally about ⅛ inch. The bosses 40, 42 provide a means for suspending the lens 14, 16 in front of the frame 12 for enabling water drainage. It is preferred that the lens periphery be unobstructed in order to provide adequate water drainage and anti-fog capability.

As shown in FIG. 1, it is preferred that four primary lens spacing bosses 40 be provided for each of lenses 14 and 16, such bosses being spaced around vision openings 30 and 32 so as to be located at about the four "corners" of each lens upon the attachment thereof to frame 12. As a result, there are two upper primary lens spacing bosses 40 and two lower primary lens spacing bosses for each lens. Spaced intermediate, each pair of upper primary spacing bosses 40 for each of lenses 14 and 16, is one of secondary spacing bosses 42. Similarly, one of secondary spacing bosses 42 is located intermediate each pair of lower primary spacing bosses 40. A total of four secondary lens spacing bosses 42 is thereby provided. Preferably, as shown in FIGS. 1 and 2, each secondary lens spacing boss 42 is spaced about ⅓ to ½ the distance between its associated innermost and outermost primary spacing bosses 40. In combination, the primary and secondary bosses 40, 42 also provide lens spacing means, or an air gap 46, for enabling water drainage from between the lens 14, 16 and the wearer's eyes (not shown).

Each of primary mounting bosses 40 is formed with a forwardly-opening, cylindrical lens mounting recess 48 (FIGS. 2 and 4) which extends rearwardly into, but preferably not through, underlying regions of frame 12. There is connected to each of lenses 14 and 16 four corresponding lens attachment pins 50 (FIGS. 1, 2 and 4). Lens attachment pins 50 preferably are nail-head shaped and extend about ⅜ of an inch in a rearward direction through lenses 14 and 16 in locations corresponding to the locations of recesses 48 in primary lens spacing bosses 40. It is preferred that the rearwardly extending portions of mounting pins be flared at least slightly outwardly and that the pins and mounting recesses 48 be relatively sized so that the pins fit tightly into the recesses. Since frame 12 is constructed of a resilient plastic or rubber, the protruding regions of pins 50 can be forced with a little pressure into the recesses so that the lenses are securely mounted to frame 12.

It should be appreciated that separable bosses 52, as shown in FIG. 5, may be utilized to space the lens 14, 16 from the frame 12. In this instance, the pin is operable for both holding the lens 16 and the boss 52 to the anterior surface 20.

It can be appreciated that lenses 14 and 16 can easily be removed from frame by pulling pins 50 from recesses 48. Alternatively, if flexible pins 50 are utilized, the lens 14, 16 may be removed by pulling the lens off the pins 50, leaving the pins 50 attached to the frame 12. As a result, different types of lenses can be used interchangeably with frame 12. For example, tinted or mirrored lenses 14 and 16 can be attached to frame 12 when goggles 10 are to be used in bright sunlight. For wearing in darker conditions, the tinted or mirrored lenses can be easily replaced by clear or less heavily tinted lenses. Similarly, thicker optically corrected lens and more protective lenses can replace thinner lenses when warranted by different conditions. Sports goggles 10 can thus be sold as a kit with a single frame 12 and two or more different types of lenses 14 and 16.

It can be seen from FIG. 4 that secondary lens spacing bosses are important in maintaining air gap 46 when frame 12 is flexed into a smaller-than-normal radius, for example, when goggles 10 are worn by an individual with a relatively small-sized head.

From the foregoing, it is apparent that more than four primary spacing bosses 40 and more than two secondary spacing bosses 42 may be provided for each of lenses 14 and 16. However, the number of primary lens spacing bosses 40 used to mount lenses 14 and 16 to frame 12 should not be so many as to make the frame too resistant to bending. Likewise, it is preferred to keep the number of secondary lens spacing bosses 42 to a relatively small number so as not to restrict the free flow of air through air gaps 46.

Strap 18 which may be formed from any suitable material and may provide additional flotation, may be attached to frame 12 in any part of the frame. However, it is preferred to make strap 18 separate from frame 12 so that it can be made more elastic and can be replaced if necessary. One manner of attaching strap 18 to frame 12 is illustrated in FIGS. 1 and 2. Two vertical slots 54 are formed in frame 12, one such slot being rearward of each vision opening 30 and 32, the height of each such slot being slightly greater than the width of strap 18 so that the strap can be passed therethrough. Ends of strap 18 are then looped a corresponding one of slots 54 and vision opening 30 or 32, as the case may be. One end of strap 18 may be attached, as by a large "rivet" 56, to an overlying region of the strap after the end has been looped through its slot 54 and vision opening 32. The other end of strap 18 may be attached (by another rivet 56) at a length-adjusting buckle 60 after being passed through its associated slot 54 and vision opening 30 (FIG. 1). Tightness of strap 18 can then be adjusted by sliding strap 18 through buckle 60.

From the foregoing detailed description, it can be appreciated that sports goggles 10 are not only rugged and have easily replaceable and interchangeable lenses, but the construction enables the goggles to be relatively easily and inexpensively made.

Although there is described above a specific arrangement of a sports goggle in accordance with the present invention for the purpose of illustrating the manner in which the invention can be used to advantage, it is to be appreciated that the invention is not limited thereto. Accordingly, any and all variations and modifications which may occur to those skilled in the art are to be considered to be within the scope and spirit of the invention as defined by the appended claims.

What is claimed is:

1. A sports goggle for water sports, downhill skiing and other sports, said sports goggle comprising:
   a. a frame having left and right vision openings and having an anterior surface and a posterior surface, said frame being constructed of a resilient and flexible material so as to enable said posterior surface to fit relatively closely to a wearer's face when the goggles are worn with the left and right vision openings in front of the wearer's respective left and right eyes;
   b. at least one lens contoured and sized for covering said vision openings in said frame, said at least one lens including left and right individual lenses sized and contoured to cover a corresponding one of said left and right vision openings in the frame;
   c. combination lens attaching and primary lens spacing means for detachably attaching said at least one lens to the anterior surface of the frame in a spaced apart relationship in order that said at least one lens covers said left and right vision openings, said combination lens attaching and primary lens spacing means include at least four mounting bosses for each of said lenses, said mounting bosses extending forwardly from said frame anterior surface around each of said vision openings, each of said mounting bosses being formed with a forwardly-opening recess, said combination lens attaching and primary lens spacing means further including rearwardly projecting attachment pins mounted to each of said left and right lenses in locations corresponding to said mounting bosses, said lenses being attached to said frame by the forced insertion of said pins into said recesses; and
   d. secondary lens spacing means for enabling said at least one lens to maintain said spaced apart relationship with the anterior surface of the frame after the attachment of said at least one lens thereto, thereby assuring an air gap between said at least one lens and underlying regions of said anterior surface of the frame.

2. The sports goggles as claimed in claim 1, wherein said combination lens attaching and primary lens spacing means comprise two spaced apart upper and two spaced apart lower mounting bosses for each of said left and right lenses, and wherein said secondary lens spacing means include at least two spacing bosses for each of said left and right lenses, said spacing bosses projecting forwardly from the anterior surface of said frame, at least one of said spacing bosses being positioned between the two upper mounting bosses for each of said lenses and at least one of said mounting bosses being positioned between the two lower mounting bosses for each of said lenses.

3. A sports goggle for water sports, downhill skiing and other sports, said sports goggle comprising:
   a. a frame having left and right vision openings and having an anterior surface and posterior surface, said frame being contoured and constructed of a resilient and flexible plastic or rubber material so as to enable said posterior surface to fit relatively closely to a wearer's face when the goggles are worn with said left and right vision openings in front of the wearer's respective left and right eyes;
   b. left and right lenses contoured and sized for covering a respective one of said left and right vision openings in said frame;
   c. combination lens attaching and primary lens spacing means for detachably attaching said left and right lenses to the anterior surface of the frame spaced outwardly therefrom and so that said lenses cover a respective one of said left and right vision openings in the frame, said combination lens attaching and primary lens spacing means including a plurality of lens mounting bosses projecting forwardly from said frame anterior surface around each of said vision openings, said mounting bosses being formed having forwardly-opening recesses therein, and further including a like plurali of pins which project rearwardly from a posterior surface of each of said left and right lenses, said pins being sized and positioned for inserting into said recesses to detachably attach said lenses to said goggles frame;
   d. secondary lens spacing means, including a plurality of forwardly extending projections formed on the anterior surface of the frame intermediate at least some of the mounting bosses for each of said left and right lens, for helping to maintain said left and right lenses spaced forwardly of said anterior frame surface after the attachment of said lenses thereto, so as to provide an air gap between each of said lenses and underlying anterior surface regions of said frame to keep the lenses from getting fogged up during use of the goggles; and
   e. resilient strap means connected to said goggle frame for retaining said goggles on a wearer's head.

4. The sports goggles as claimed in claim 3, wherein one of said spacing bosses is positioned between the two upper mounting bosses for each of said left and right lenses and at least another one of said mounting bosses is positioned between the two lower mounting bosses from each of said left and right lenses.

5. The sports goggles as claimed in claim 3, wherein all of the mounting and spacings bosses have substantially the same height above the anterior surface of the frame.

6. The sports goggles as claimed in claim 3, wherein said frame is constructed of a lightweight non-water permeable material which enables said goggles to float in water, and wherein said lenses are constructed of a thin, flexible, impact resistant transparent lens material.

* * * * *